United States Patent
Soliz (10) Patent No.: US 8,868,157 B1
(45) Date of Patent: Oct. 21, 2014

(54) THERMAL OPTICAL IMAGER SYSTEM AND METHOD FOR DETECTION OF PERIPHERAL NEUROPATHY

(71) Applicant: VisionQuest Biomedical, LLC, Albuquerque, NM (US)

(72) Inventor: Peter Soliz, Albuquerque, NM (US)

(73) Assignee: VisionQuest Biomedical LLC, Albuquerque, NM (US)

( * ) Notice: Subject to any disclaimer, the term of this patent is extended or adjusted under 35 U.S.C. 154(b) by 68 days.

(21) Appl. No.: 13/672,590

(22) Filed: Nov. 8, 2012

Related U.S. Application Data (60) Provisional application No. 61/557,816, filed on Nov. 9, 2011.

(51) Int. Cl.
    *A61B 6/00* (2006.01)
    *A61B 5/00* (2006.01)
    *A61B 5/103* (2006.01)

(52) U.S. Cl.
    CPC .................. *A61B 5/0077* (2013.01)
    USPC ............ 600/474; 600/475; 600/549; 600/592

(58) Field of Classification Search
    USPC .................. 600/473–475, 549, 592; 349/199
    See application file for complete search history.

(56) References Cited

U.S. PATENT DOCUMENTS

| | | |
|---|---|---|
| 4,327,742 A | 5/1982 | Meyers et al. |
| 4,327,743 A | 5/1982 | Katz |
| 5,124,819 A | 6/1992 | David |
| 5,678,566 A | 10/1997 | Dribbon |
| 6,090,050 A | 7/2000 | Constantinides et al. |
| 6,640,130 B1 | 10/2003 | Freeman et al. |
| 2007/0043408 A1 | 2/2007 | Winnett |
| 2007/0211355 A1 | 9/2007 | Dalbo et al. |
| 2010/0041998 A1 | 2/2010 | Postel |

FOREIGN PATENT DOCUMENTS

| | | |
|---|---|---|
| EP | 0885587 | 12/1998 |
| EP | 1511419 | 8/2008 |
| WO | 03/002186 | 1/2003 |
| WO | 2005/118516 | 12/2005 |
| WO | 2012/051394 | 4/2012 |
| WO | 2012/135365 | 10/2012 |

OTHER PUBLICATIONS

Bagavathiappan, Subramnaiam et al., "Correlation between Plantar Foot Temperature and Diabetic Neuropathy: A Case Study by Using an Infrared Thermal Imaging Technique", Journal of Diabetes Science and Technology vol. 4, Issue 6, 2010, 1386-1392.

Benbow, Susan J. et al., "The Prediction of Diabetic Neuropathic Plantar Foot Ulceration by Liquid-Crystal Contact Thermography", Diabetes Care, vol. 17 No. 8, 1994, 835-839.

Bharara, M. et al., "Cold Immersion Recovery Responses in the Diabetic Foot with Neuropathy", Int Wound J., vol. 5 No. 4, 2008, 562-569.

(Continued)

*Primary Examiner* — Michael Rozanski
(74) *Attorney, Agent, or Firm* — Peacock Myers, P.C.; Janeen Vilven (57) ABSTRACT

A system and method for assessing a peripheral neuropathy risk wherein the system and method according to one embodiment of the present invention detects abnormality which may be directed to a probability, a stage, a category, or other indicator as to the degree of progression of the disease.

12 Claims, 10 Drawing Sheets
(4 of 10 Drawing Sheet(s) Filed in Color)

(56) References Cited

OTHER PUBLICATIONS

Bharara, M. et al., "Thermography and Thermometry in the Assessment of Diabetic Neuropathic Foot: A Case for Furthering the Role of Thermal Techniques", Lower Extremity Wounds vol. 5, No. 4, 2006, 250-260.

Bharara, Manish et al., "Coming events cast their shadows before: detecting inflammation in the acute diabetic foot and the foot in remission", Diabetes Metab Res Rev 28, 2012, 1-5.

Bharara, Manish et al., "Wound Inflammatory Index: A "Proof of Concept" Study to Assess Wound Healing Trajectory", J Diabetes Sci Technol. vol. 4 No. 4, 2010, 773-779.

Burge, Mark R. et al., "Potential for using functional thermal imaging to detect early signs of peripheral neuropathy", www.DiabetoValens.com, 2012, 1.

Roback, Kerstin, "An overview of temperature monitoring devices for early detection of diabetic foot disorders", Expert Rev. Med. Devices 7(5), 2010, 711-718.

Stess, Richard M. et al., "Use of Liquid Crystal Thermography in the Evaluation of the Diabetic Foot", Diabetes Care, vol. 9 No. 3, 1986, 267-272.

Veikutis, V. et al., "Clinical identification of early "diabetic foot" by infrared imaging", Conference "Biomedical Engineering", 77-80.

THERMAL OPTICAL IMAGER SYSTEM AND METHOD FOR DETECTION OF PERIPHERAL NEUROPATHY

CROSS-REFERENCE TO RELATED APPLICATIONS

This application claims priority to and the benefit of the filing of U.S. Provisional Patent Application Ser. No. 61/557,816, entitled "Thermal Optical Imager System and Method for Detection of Peripheral Neuropathy", filed Nov. 9, 2011, and the specification is incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Thermal (functional) imaging can show anatomically relevant information that is useful in assessing local and regional function of the neuronal network. Performing regional analysis of the effects of cold provocation on the body is important in the evaluation of diabetic peripheral neuropathy. A thermal image video presents information about the components that contribute to the bioheat transfer for a particular region affected by damaged neurons in that region of the body. When cold challenged, the thermal pattern of the toes and plantar regions of the foot and hands will reveal a spatial and temporal depiction of the neuronal function/activity of the foot or hand as it modifies the thermoregulatory system when imaged in the infrared wavelengths. The thermal images obtained contain information not currently analyzed for a relationship of these parameters (spatial and temporal) that correlate to the risk of onset, or increase in, the level of peripheral neuropathy.

U.S. Pat. No. 5,678,566 to Dribbon, describes the potential of infrared (thermal) imaging as a diagnostic tool for diabetic foot (peripheral neuropathy). Prior patents measure visual patterns of infrared thermal emissions from various regions of the body employing thermochromic liquid crystal technology (TLC) (See U.S. Pat. No. 5,124,819 to Davis, U.S. Pat. No. 5,678,566 to Dribbon, U.S. Pat. No. 4,327,742 to Meyers et. al., and U.S. Pat. No. 4,327,743 to Katz). TLC technology comes with a number of inherent limiting factors. Microencapsulation process is often used to reduce the degradation of pure TLC materials, which are organic compounds that easily degrade when exposed to chemical contamination and to ultraviolet (UV) light. Additionally, before the TLC can be used for the temperature measurement, a hue-temperature calibration must be conducted. This calibration must be repeated frequently.

It is well known that the lighting angle and the coating thickness significantly affects the TLC hue-temperature calibration curves, and a complete understanding on how the temperature measurement uncertainty of the TLC is influenced by those factors is a significant limitation.

Prior disclosures have failed to optimize the device so that (i) the temporal and spatial temperature changes represented by color changes would be readily quantifiable nor the processed data readily presented to the medical technician or physician; (ii) the design of the system would facilitate its use as a tool for contra-lateral comparison and visual examination by the foot care specialist in a diabetic foot screening environment; and (iii) these past systems have not presented a means or analytical technique to quantify the level of risk of a asymptomatic diabetic patient.

These prior devices and techniques used to obtain thermal, infrared emission measurements were not designed specifically for risk stratification of diabetic patients who present without symptoms of loss of neuronal function as a precursor to peripheral neuropathy. These prior devises fail to present a model for interpreting the results of the thermal measurements. These prior devices fail to combine new thermal detectors with a clinical procedure for stimulating homeostasis and measuring the related neuronal function.

A number of research papers have been presented on various aspects of use of LCT technology for peripheral neuropathy. See Bharara et al.: "Thermoography and Thermometry in the Assessment of Diabetic Foot: A Case for Furthering the Role of Thermal Techniques," Lower Extremity Wounds 5(4); 2006, 250-260; Bharara et al.: "Cold Emersion Recovery Responses in the Diabetic Foot with Neuropathy," International Wound Journal, 2008, 5:562-569; Stess et al.: "Use of Liquid Crystal Thermography in the Evaluation of the Diabetic Foot," Diabetes Care., 9(3):267-272 (May-June, 1986); Benbow et al.: "The Prediction of Diabetic Neuropathic Plantar Foot Ulceration by Liquid-Crystal Contact Thermography," Diabetes Care, 17(8)835-639 (August, 1994). These papers and others limit their discussion to LCT. They measure static conditions and not dynamic, functional signals. They describe signals from advanced conditions when a patient has already developed peripheral neuropathy.

According to the Center for Disease Control (CDC), diabetes afflicts an estimated 171 million people worldwide, including more than 24 million Americans. Diabetic patients are at risk for a wide array of complications including heart disease, kidney disease (nephropathy), ocular diseases (diabetic retinopathy), and peripheral neuropathy (diabetic foot).

It is estimated that 60-70% of diabetics have some degree of neuropathy. Fifteen percent, two million, of these will develop a foot ulcer during their lifetime. Foot ulcers are the main cause, 85%, of lower extremity amputation in patients with diabetes. Neuropathy is one cause for the impairment thermoregulatory function including bioheat production by metabolic processes in the diabetic foot. Patients with long-standing neuropathy will have poor regulatory mechanisms and hence altered microcirculatory dysfunction. This condition is linked to neuropathic complications that alter the regulatory mechanisms controlling heat production in the peripheral neuropathy.

82,000 amputations are performed annually on diabetics. Studies have shown that about 5% of diabetic patients will develop a foot ulcer in a given year. Fifteen percent of diabetics will undergo amputation sometime in their lives. Foot pathology accounts for 25% of all hospital stays among people with diabetes, and the cost of foot disorder diagnosis and management are estimated at $10.9 billion dollars annually.

Economically, treatment and other costs attributable to peripheral neuropathy would be reduced significantly if the U.S. population of diabetics were screened, preclinical signs of peripheral neuropathy were identified, and these individuals would undergo educational intervention. Identification of the "at risk" foot prior to the onset of altered foot anatomy or clinically significant peripheral vascular disease will allow for the institution of preventative measures and vigilant surveillance that may alter the natural history of this most-feared complication of diabetes and save millions of dollars in annual healthcare costs.

It is recommended that all patients with diabetes have a thorough pedal examination at least once a year, even if no signs of neuropathy are present. Clinical testing may include a number of tests, some of which present inter- and intra-observer variability, such as vibration sensation applied by a tuning fork test or pressure sensitivity as applied by a monofilament test. Others are expensive or are invasive such as the ankle brachial index, transcutaneous oxygen measurements, pulse volume recordings, laser Doppler flowmetry and/or nerve conduction tests. As a result, longitudinal assessment of progression or treatment (therapeutics) it is nearly impossible except where significant changes occur. Today an instrument that gives a preclinical indication of risk for onset of neuropathy is not available.

One function of the neuronal system is the control of capillaries as a means for thermoregulation to maintain body temperature through heat exchange processes. The capillary flow is controlled by thermoreceptor signals that trigger the vasodilatory response in the skin. This is an auto-regulatory mechanism triggered by thermal stress. Dysfunction of this process can signal the presence of peripheral neuropathy. Cold and warm receptors are located at a depth of tenths of millimeters and are activated with changes in surface temperature, which are easily visible as far infrared i.e., thermal, emission.

Oxidative stress has been associated with the pathogenesis of many diseases, including diabetes and cardiovascular disease. This state is caused by an imbalance of oxidants and antioxidants, wherein the body can no longer repair damage from naturally occurring by-products of oxidation, such as free radicals. Endothelial cells are among the structures damaged, affecting the production of endothelium-induced nitric oxide (eNOS), a signaling molecule essential to proper regulation of the vasculature. To compensate, the body will produce inducible nitric oxide (iNOS). However, iNOS produced in an oxidative environment will combine with the free radical superoxide to produce high levels of peroxynitrite, moving the body into a state of nitrosative stress. Sustained nitrosative stress can lead to peripheral nerve damage and, eventually, nerve death.

Depending on its severity, nerve damage can manifest as a hypothermic or hyperthermic area on an infrared image. Both endothelial dysfunction and peripheral nerve damage have been associated with vasoconstriction, which would produce hypothermic areas in an infrared image. As damage to the sympathetic nervous system progresses, these areas will begin to appear hyperthermic, as chronic inflammation is associated with irreversible nerve damage and impending cell death.

Although thermal imaging has been used for structural imaging of the diabetic foot, these studies have focused only on discovering absolute skin/tissue temperature differences between individuals. Investigators hypothesized that differential spatial temperature characteristics in affected regions of the body were early indications of peripheral neuropathy, and they hoped that abnormal capillary function in the affected regions could be detected. The significance and value of this approach to diagnosing or staging peripheral neuropathy has come into question by a number of investigators.

Bharara, et al. studied cold immersion recovery response for diabetics with peripheral neuropathy. Bharara et al. describe a very different thermal measurement device based on thermochromic liquid crystals (TLC). The Bharara system is inherently limited and not able to measure temporal fluctuations at rates of greater than about 1 Hz. TLCs are not thermal imagers in the sense of infrared devices. These are liquid crystals that change color as a function of temperature and must be interpreted off-line. Lack of temperature precision is due to the need for the interpretation of the color displayed. TLC technology was appropriate to meet Bharara's goal for only measuring an initial temperature and a recovery temperature. Rapid measurements over an extended period of time is not feasible with TLC technology nor contemplated by Bharara.

Infrared imaging is a modality that has been misrepresented in the popular imagining. For example, if one were to point an infrared camera through a window at a bright sunny scene outside, the result would be a black featureless image. Window glass absorbs all infrared light and transmits none. The color of an object to our eye is uncorrelated to its infrared color (emissivity and temperature). Factors that may affect other measurement approaches, such as tissue thickness and pigmentation, are not major contributors to the measured thermal emission.

Memarian et al., state, "thermography is skin color invariant since there is no difference in emissivity between black, white and burnt skin, in vivo or in vitro. Human skin has an emissivity of about 0.98. Thermal radiation from the skin originates in the epidermis and is independent of race; it depends therefore only on the surface temperature. Secondly, thermal image quality is independent of ambient lighting conditions and can thus be effective both night and day." As explained above, skin pigmentation is not the dominant term in thermal emission. The energy radiated by a blackbody radiator per second per unit area is given by $\epsilon\sigma T^4$ where $\epsilon$ is the emissivity (0.98 for human tissue), $\sigma$ is the Stefan-Boltzman constant ($5.6703\times10^{-6}$ watts/m$^2$K$^4$), and the temperature, T, is in degrees Kelvin. $\epsilon$ is a linear factor in the thermal emission, while temperature is to the fourth power. From the Stefan-Boltzman relationship, the small variation in $\epsilon$ due to pigmentation is not a major contributor to the measured thermal emission.

Figure 1:
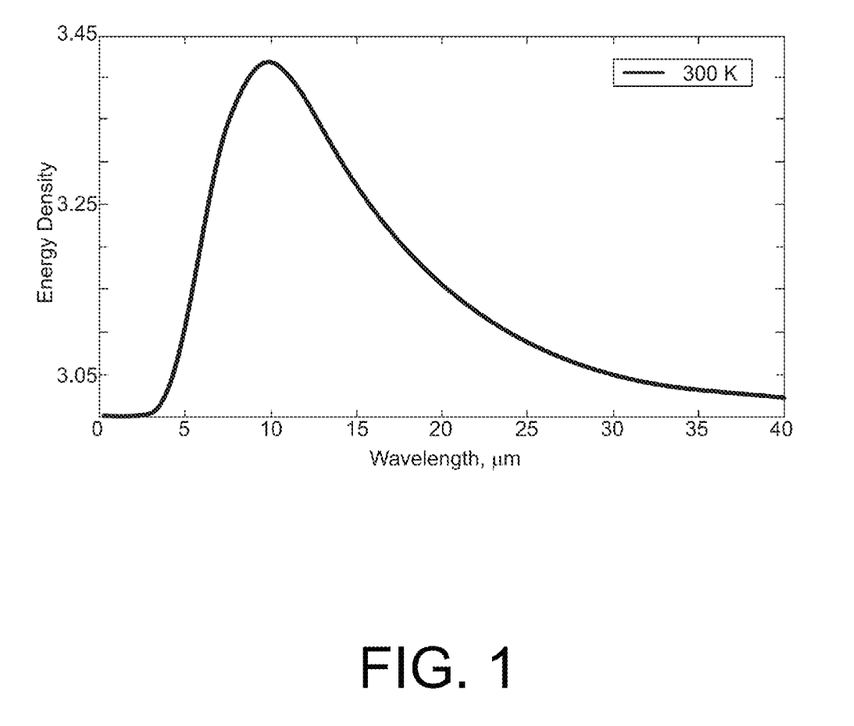
FIG. 1 presents the black body radiation from a typical human at 310° K.

The normal body core temperature stays at a constant 37° C. or about 310° K. FIG. 1 shows the radiative emittance for a black body (emissivity=1) for the typical human skin regardless of race. Note that the emissivity is at a near maximum in the far infrared (8 to 12 micrometers).

Figure 2:
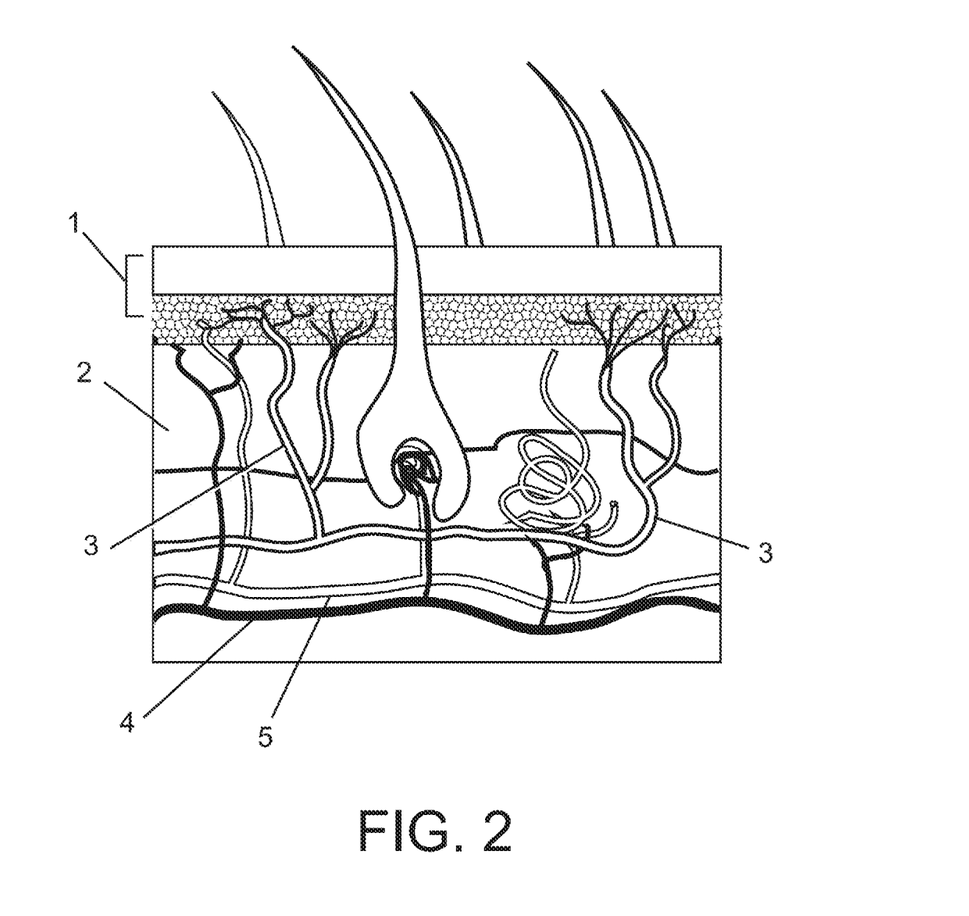
FIG. 2 shows the structure of the outer layers of the human skin.

Tissue thickness values of about 11.05, 7.85, 6.65, 6.55, and 5.05 mm for metatarsal heads 1 through 5, respectively, have been reported. The signal that is observed is dominated by the heat transfer from the capillaries to the surrounding plantar tissue. That capillary bed is found between about 0.6 and about 1.0 mm from the surface of the skin (see FIG. 2, element 1). Both visible and infrared signals can measure changes in the microvascular function at this depth.

The passive thermoregulatory system is modeled using the Pennes bioheat equation. Pennes' bioheat equation is based on the regular heat diffusion equation but where an additional isotropic source term has been added to account for the heat transported by blood in the surrounding tissues. The Pennes bioheat equation is given by $$\nabla \cdot k \nabla T + \rho_{bl} w_{bl} c_{bl}(T_{bl,a} - T) + q_m = \rho c \frac{\partial T}{\partial t}$$

where k is the thermal conductivity of the tissue, T is the temperature of the tissue, $\rho_{bl}$ is the blood density, $w_{bl}$ is the volumetric rate of blood perfusion to the tissue per unit volume, $c_{bl}$ is the blood specific heat, $T_{bl}$, is the arterial blood temperature of the tissue, $q_m$ is the rate of metabolic heat production per unit volume, $\rho$ is the tissue density, c is the tissue specific heat, and t is time. The perfusion heat source term assumes that all the heat transfer to the tissue takes place a few millimeters from the skin surface within the capillary bed.

This heat transfer equation does not require explicit knowledge of the blood perfusion, nor blood flow. Therefore, the infrared measurements showing changes in radiative emission of the skin surface can be deduced to be a result of the auto-thermoregulation instigated by the functional integrity of the neuronal network.

BRIEF SUMMARY OF THE INVENTION

According to one embodiment of the present invention a method of detecting a neuronal health of a patient's foot is provided. The entire plantar and dorsal foot is monitored with a infrared detector. Preferably, the detector is not a TLC imager. A pre-treatment temperature of the selected locations of the patient's foot being monitored is obtained. For example, the image obtained and the temperature measure changes for the entire foot, including sole (plantar) and top (dorsal). Information about the health of the foot depends not just on local time changes, but spatial variations in the change. A cold pressor is applied to the patient's foot for a predetermined amount of time to reduce the temperature in the patient's foot to a temperature of between about 90° F. and 60° F. preferably not less than about 75° F. However, the temperature depends on the individual. A cold pressor can be as cold as 40° F. to 50° F. and applied for about a minute. The cold pressor is removed from the patient's foot. A plurality of images of the patient's foot is obtained using an infrared imager having a data acquisition rate between about 10 Hz and 60 Hz capture an increase of surface temperature of the patient's foot over a pre-determined amount of time after the cold pressor is removed from the patient's foot. For example, acquisition of the plurality of images begin immediately after removal of the cold pressor. The plurality of images obtained are coregistered. Registration is a term used in image processing and is synonymous with alignment. All images in the video may be co-aligned to make measurement on the same region of the foot throughout the experiment. A time course for the increase of surface temperature of the patient's foot during a predetermined time course following removal of the cold pressor is recorded. For example the locations of the patient's foot being monitored include the plantar and dorsal portions of the foot or any section thereof. A rate of temperature recovery of the patient's foot during the first minute following cold pressor removal and a total time for the patient's foot to recover to a pre-treatment temperature is determined. For example, the first minute will yield one characteristic or feature that will help identify neuropathy. In the course of the 15 minutes, other features will present themselves. The rate of temperature recovery of the patient's foot and total time for the patient's foot to recover to a pre-treatment temperature to the rate of temperature recovery of a normal control foot and total time to recover to a pre-treatment temperature of a normal control foot is compared to determine the neuronal health of the patient's foot. For example a control foot is a term to describe a response measured according to one embodiment of the present invention from a subject's foot when the subject's peripheral neurological system and vascular system is intact and/or health is otherwise considered normal. The control may be the same sex, and similar as to other metrics such as weight, height, age, and/or race for example. If a patient being monitored doesn't achieve a level of recovery comparable to control, then he/she may be identified as at risk for neuropathy. Further, the registering step may comprise aligning a fiduciary within each image for use in co-registration of image frames.

In one embodiment the infrared imager comprises an infrared detector.

In another embodiment a temperature measuring device to detect regions of thermal emission variations of the plantar of the foot is employed.

According to one embodiment, the images are obtained in the approximately 500 nm to 900 nm spectral range.

Further scope of applicability of the present invention will be set forth in part in the detailed description to follow, taken in conjunction with the accompanying drawings, and in part will become apparent to those skilled in the art upon examination of the following, or may be learned by practice of the invention. The aspects. objects and advantages of the invention may be realized and attained by means of the instrumentalities and combinations particularly pointed out in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

Additional objects, aspects, and advantages of the present invention will be apparent in the following detailed description read in conjunction with the accompanying drawing figures.

DETAILED DESCRIPTION OF THE INVENTION

Figure 3:
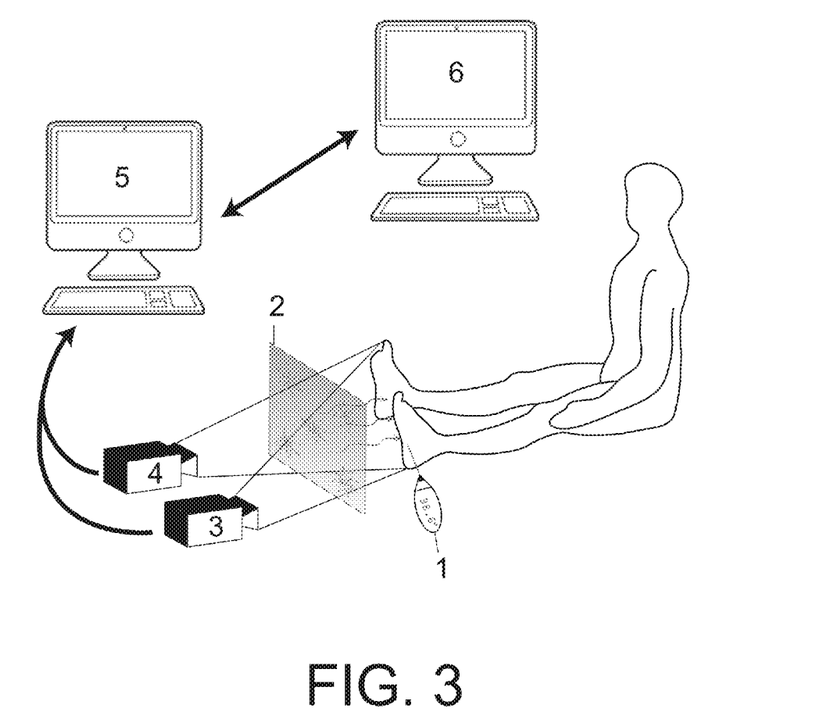
FIG. 3 presents a schematic of the embodiment of the system.

An aspect of one embodiment of the present invention provides a new thermal-optical imaging system and method for detecting and quantifying neuronal dysfunction associated with peripheral neuropathy, cardiovascular or other vascular or neuronal disease. A schematic drawing of a system according to one embodiment of the present invention is illustrated in FIG. 3.

According to one embodiment of the present invention a method for the early detection of peripheral neuropathy comprises measuring neuronal function from various anatomical regions and collecting the baseline information with an imager, such as visible light (about 400 nm to about 900 nm), near infrared (about 900 nm to about 2 micrometers), mid-infrared (about 2 micrometers to about 7 micrometers) and far infrared (about 7 micrometers to about 15 micrometers). In one embodiment the spatial and temperature recovery data is recorded with an infrared sensor operating in the near-, mid-, or far-infrared part of the electromagnetic spectrum.

In a second embodiment, spectral data are collected with standard digital imager modified by a spectral device such as optical filters to selective image in one or more narrow bands of the visible to near-infrared part of the spectrum. Further, this embodiment comprises obtaining spectroscopically metabolic status in a variety of tissues, e.g. pulse oximetry, which utilize the oxyhemoglobin (oxy-Hb) and deoxyhemoglobin (deoxy-Hb) absorption bands to estimate arterial hemoglobin oxygen saturation. Collecting spatial and temporal data provided by these devices analyzing the data to provide a status as to the health of an object.

In a one embodiment, a standard CCD camera is employed to complement the infrared data.

Embodiments of the present invention use infrared imaging to evaluate changes to the plantar foot induced by extended states of oxidative and nitrosative stress in the body.

A dynamic, functional imaging technique is different and avoids the shortcomings of static thermal measurements by applying a cold stimulus that produces a temporally and spatially varying response in the thermal auto-regulation, which has not been studied. The effect of cooling the foot's capillaries to 8 to 12° C. below the core body temperature of 37° C. is easily detected with a thermal imaging device. The spatial patterns in the time to recover to normal state are the signal that is measured and analyzed to detect preclinical stages of peripheral neuropathy.

The current invention relates to medical risk assessment and in particular the risk assessment of neuropathy for example peripheral neuropathy, or other neurological and/or vascular disease in the human extremities, such as feet and legs. One embodiment of the present invention is an apparatus to perform functional imaging of the plantar foot or hand to establish the viability or condition of the thermoregulatory system in the human body, especially as reflected in the neuronal function in the extremities of the body.

In a further embodiment, imaging in the approximately 500 to 900 nm spectral range can yield information about the function of the neuronal network as it compromises the auto-thermoregulation affecting the tissue surface and sub-layers.

Embodiments of the present invention are useful in high volume use and diagnosis, such as needed in a clinical setting of an endocrinologist and/or as a low-cost instrument for screening where a diagnosis is not immediately required.

An aspect of an embodiment of the present invention provides a thermal-optical imaging system for detecting and quantifying neuronal and microvascular dysfunction associated with peripheral neuropathy. An aspect of a method according to one embodiment of the present invention is a novel imaging protocol that will measure function and structural patterns in a diabetic patient's foot.

Figure 7:
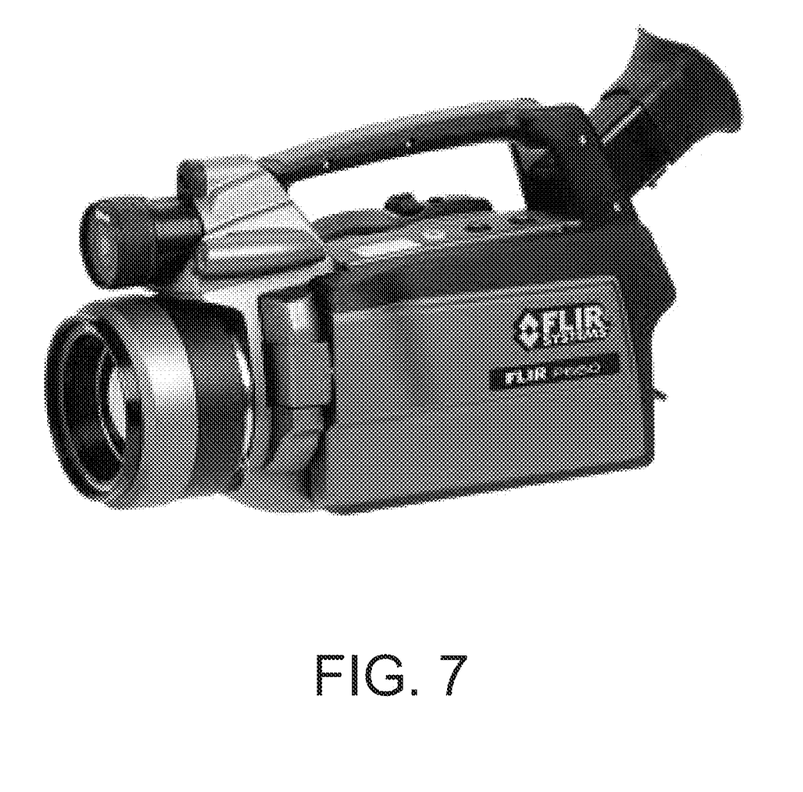
FIG. 7 shows a picture of an FLIR 660 video camera according to one embodiment of the present invention.

Another embodiment of the system comprises a camera that combines two of the modalities, for example shown in FIG. 7 is a FLIR B660 (far infrared) and a digital video camera. The thermal component of the B660 imager operates in the 7.5 to 13 µm area of the infrared spectrum. At these wavelengths one is measuring the thermal emission from the field of view in an anatomical region for example the plantar region of a subject's foot. A FLIR thermal camera comprises a data acquisition system that makes the imaging ready to operate.

The second component is a digital camera that is integrated into the same device and operates in the visible part of the spectrum. A band pass filter that transmits light at the 750 nm+/−10 nm collects light where changes in the optical length affect the amount of reflected light.

Figure 4:
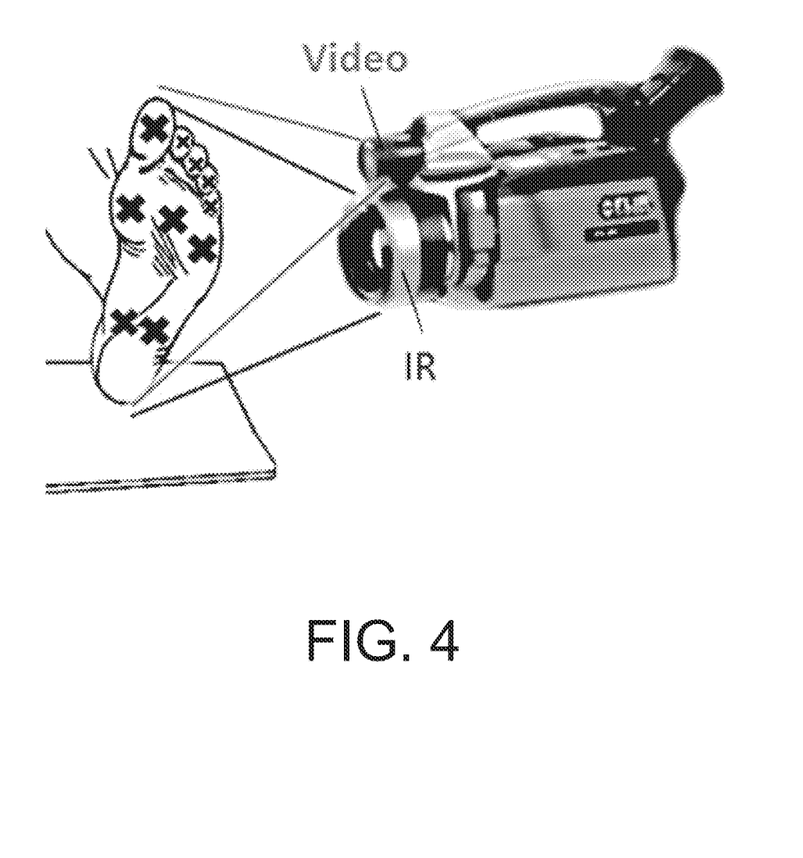
FIG. 4 is a drawing illustrating an imaging device and foot resting frame test components according to one embodiment of the present invention.

Optionally another component is a wooden foot resting frame used for the subject's comfort and alignment of the feet with one or more sensors (FIGS. 3-4).

For precise co-registration among all the video frames of a thermal imager, a fiduciary label and/or target may be placed in a field of view and a subject's foot. Alternatively, a tracking algorithm may be applied to other natural features of the foot, such as the edges of the arch, heel, or toes. This simplifies the implementation of a self-alignment procedure during the operation, as well as in the analysis of the data. A camera preferably comprises of a data acquisition system that allows rates in excess of about 10 frames per second, which captures surface temperature changes.

EXAMPLE

Figure 5:
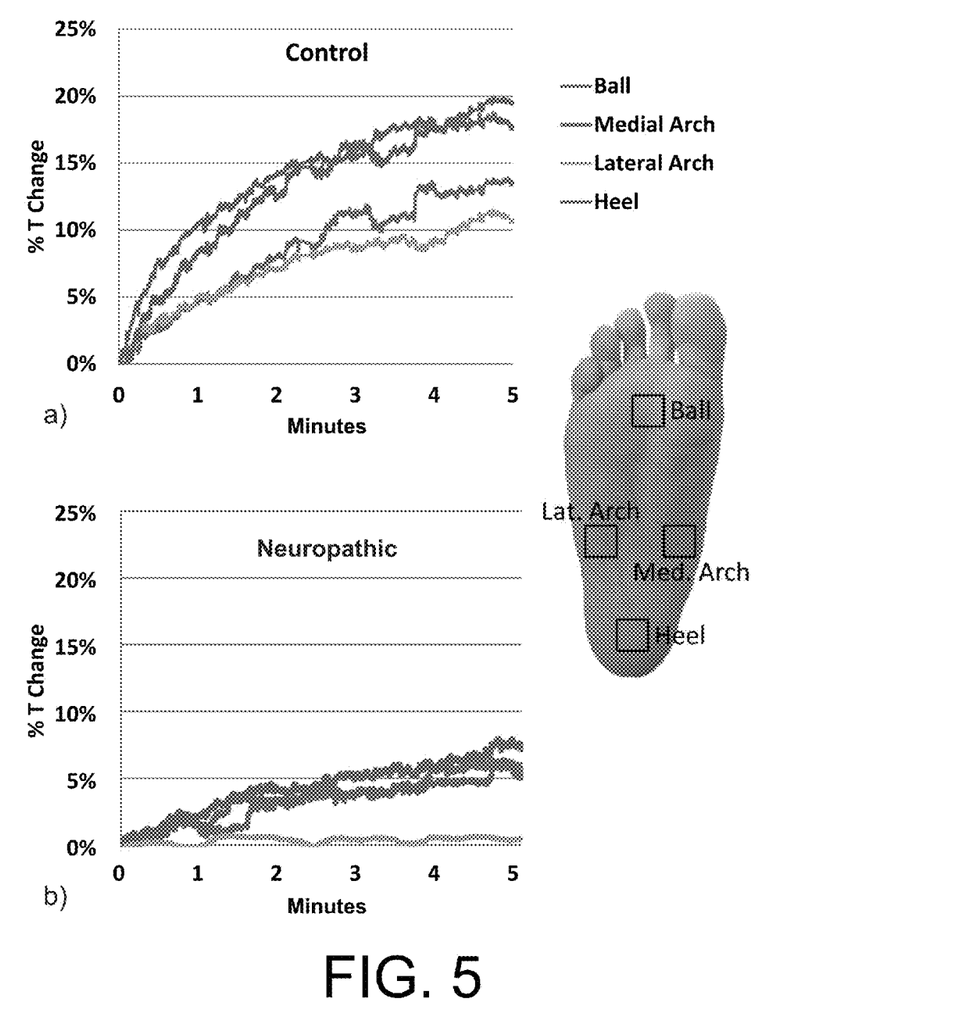
FIG. 5a presents a time sequence of a normal, healthy control subject's recovery after the cold pressor is applied. Four points on the plantar foot are shown, the lateral arch, the medial arch, the heel, and the ball.
FIG. 5b shows a time sequence of a peripheral neuropathy patient prior to the cold pressor application, then at 2, 4 and 5 minutes post cold pressor test.
Figure 6:
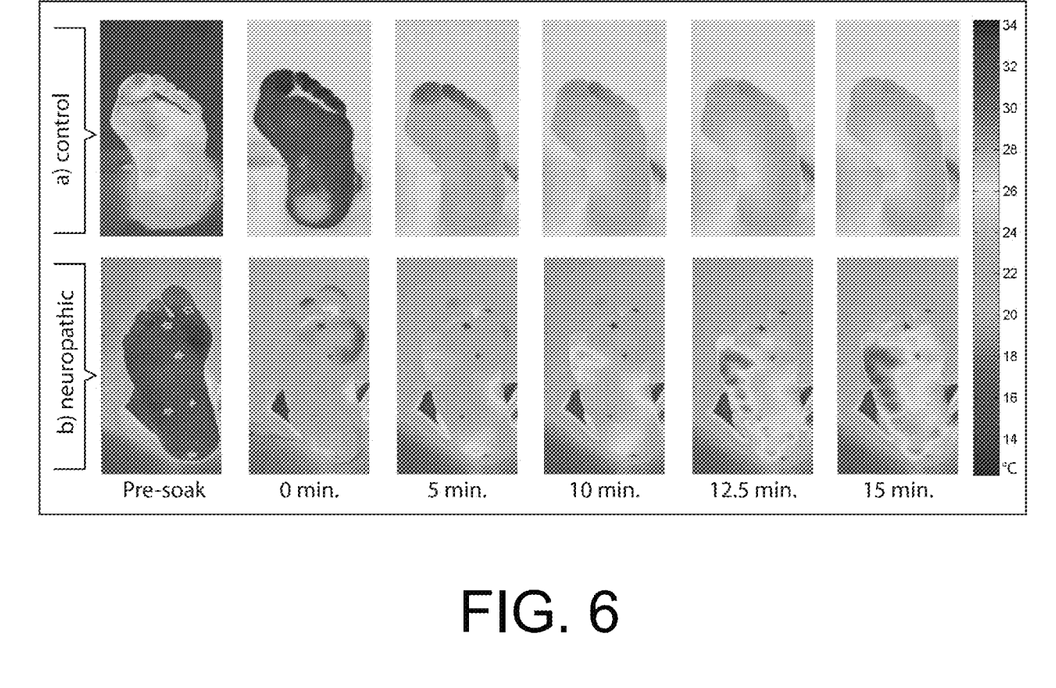
FIG. 6 illustrates six frames in a 15 minute time sequence post cold pressor test

FIG. 5 was captured immediately after the removal of a cold patch. Note that the region from the heel has been cooled below the temperature of the other regions of the same foot and shows a clear temperature difference from the right (un-cooled) foot (blue is cooler than the yellow and red in this color scheme). FIG. 6 was captured at about 2 to about 5 minute intervals after removal of the cold pressor patch.

Figure 8:
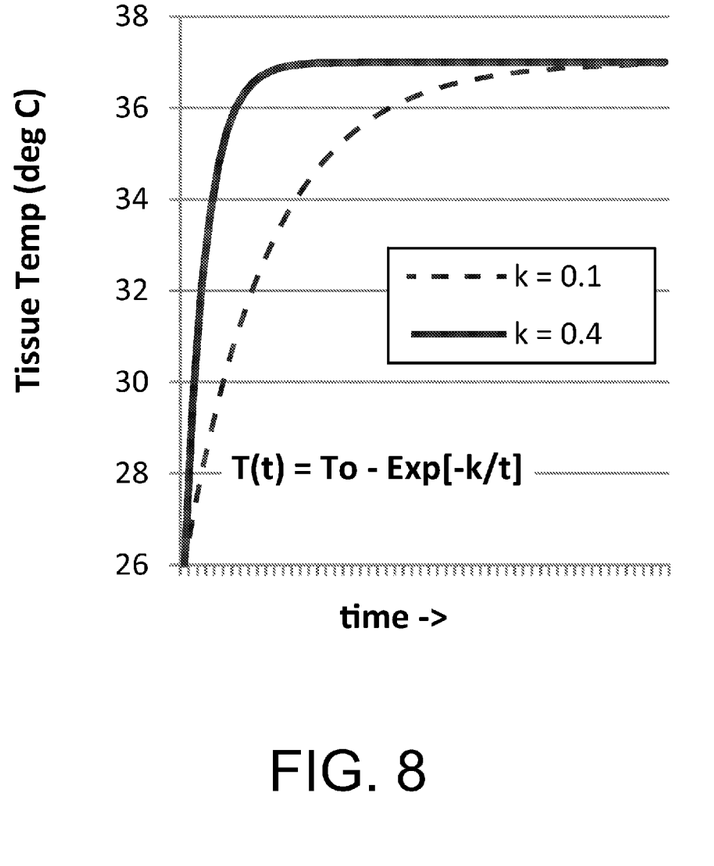
FIG. 8 is a graph of the temperature recovery rate using one type of mathematical function, an exponential.

The thermal and spectral videos are analyzed in two ways. Referring now to FIG. 5, in this example four points on the foot are marked for producing a temporal plot of the temperature over the period of the recording as is illustrated in this example. Samples are taken at the five phalangeal points on the foot and five other locations of the foot. The number of pixels and resolution allow us to average a sample area of no less than about 5×5 pixels (25 pixels) to remove any noise in the data. For each point a curve fit of the data using the model shown in FIG. 8, $$T(t) = T_0 - \mathrm{Exp}[-\kappa t],$$

where the thermal measurement as a function of time, T(t), is modeled by the initial thermal temperature minus the exponential function at a time, t, and for the recovery factor, K. For example, our analysis models not only the general recovery factor, but the spatial variation of the recovery factor.

As mentioned previously, the signal that is being measured is based on a difference in metabolic activity between individuals. A neuropathic subject has decreased metabolic function that results in a reduced rate of recovery after the cold pressor is applied to the foot plantar. The vascularized foot plantar presents an optimal location on the body to make this measurement. It is easily accessible to an imager and minimally invasive to the patient. The thermal processes in play are conduction, advection, and radiation. First the cold pressor test transfers the cold to the foot plantar through conduction. After removal of the cold patch, advection of warm blood from the leg and body core is reduced due to the reduced flow of blood. As the capillary bed recovers, i.e. returns to normal, the advection term again is a dominant term in the thermal equation in the form of increase blood flow. The other terms are small by one or more orders of magnitude. Terms such as radiative cooling/warming, conduction with the room air (when kept at comfortable levels), and other metabolic factors such as shivering minimally affect thermal changes.

Referring now to FIG. 6 the thermal recovery pattern for both a neuropathic patient and an age-matched control (no known systemic disease) is illustrated. There are numerous methods to analyze each of the cases using both spatial and temporal information, separately or in combination. Algorithmically, one would differentiate or classify an individual as having some stage of peripheral neuropathy based on the characteristics of the temporal recovery for local regions of the plantar foot. This figure shows the recovery for six selected points on the plantar foot for the neuropathic subject. Visually there is a clear difference that would give the primary physician, such as podiatrist, an indication of peripheral neuropathy. Similarly, the recovery characteristics of the normal, control clearly show the healthy state of the neuronal network. Data obtained from a control foot or other peripheral body part similarly treated like the peripheral body part or foot of the patient being monitored is also referred to herein as a normalized control value or control.

Information obtained within images of FIG. 6 presents a means of quantitating the characteristics of the neuronal condition as presented by the recovery curves. Amplitude of the recovery is one metric. Other metrics include deviation from the modeled curve of the control.

Figure 9:
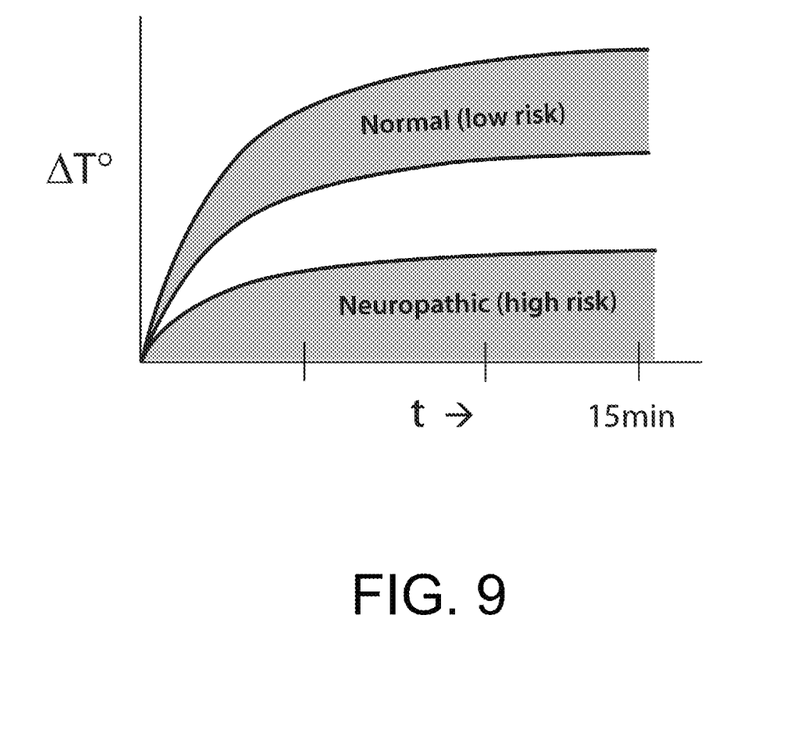
FIG. 9 depicts the risk assessment model based on a normative model and a neuropathic model where the area in grey is illustrative of the range of temperature values overtime for each group identified.

The application of these curves or the model to clinical practice depends to a great deal on the ability to develop a normative region, such as depicted in FIG. 9. This normative model is used to present to the healthcare provider a risk factor, e.g. low, medium, or high risk. This may prompt either a normal response from the physician or a referral for a complete foot examination.

The normative model is created with a statistically significant number of cases, $N \geq 500$ for a $p<0.001$ for each of three categories of subjects. The first is the gender and age-matched normal, controls. These are individuals with no known system disease. These individuals display the greatest rate of recovery when measured at least four points on the plantar foot.

The second and most extreme category is composed of those individuals with diagnosed peripheral neuropathy. These individuals have the slowest recovery rate. Recovery rates have other characteristics aside from the slow rate. Recovery can be a non-smooth function and may have a large $R^2$ (large variance from the exponential function for T(t) given above).

The third group is composed of diabetics who are not presently diagnosed with peripheral neuropathy. This group falls in the region between the two extremes. These individuals benefit from embodiments of the present invention. A risk factor is assigned to these individuals that depend on the proximity to the neuropathic region. These individuals are undiagnosed with peripheral neuropathy, but have some degree of risk depending on the characteristics of their functional recovery.

According to one embodiment, signal processing techniques are applied to the data to permit extraction of the smaller changes from the noisy background. Independent component analysis (ICA) is one of those techniques, which have previously applied in functional imaging recordings with great success in extracting small (0.1 to 1%) changes in retinal function from cats, primates, and human retinas.

ICA is a technique that attempts to extract the underlying signals of a process by using only the assumption that those signals are statistically independent. In its simplest form, a video X can be expressed as a combination of source signals S mixed by a linear mixing matrix A, as in: $X = A \cdot S$. The source signals can be thought of as the map of changes in temperature on the subject's feet, while the ICA gives the temporal response of those sources. In this embodiment, ICA is used to extract spatial and temporal functional responses of a subject's feet, and thus the sources will indicate the precise spatial location where changes are occurring, and their temporal profile.

In another embodiment, and as readily understood by one of ordinary skill in the art, an apparatus according to one embodiment of the present invention comprises a general or specific purpose computer or distributed system programmed with computer software implementing the steps described above, which computer software may be in any appropriate computer language, including C++, FORTRAN, BASIC, Java, assembly language, microcode, distributed programming languages, etc. The apparatus can optionally comprise a plurality of such computers/distributed systems (e.g., connected over the Internet and/or one or more intranets) in a variety of hardware implementations. For example, data processing can be performed by an appropriately programmed microprocessor, computing cloud, Application Specific Integrated Circuit (ASIC), Field Programmable Gate Array (FPGA), or the like, in conjunction with appropriate memory, network, and bus elements.

The Imaging Protocol

Below is an example of an embodiment of the present invention:

The imaging comprises data collected from both feet simultaneously. Both feet are allowed to warm or cool to room temperature for about 30 minutes. Room temperature is about 22 degrees Centigrade (C). Foot preparation includes removal of any significant amounts of dirt and debris from the plantar feet. Both feet are also dried to remove effects of moisture.

Feet are propped on a foot rest that removes most or all foot movement.

One or both soles of the feet are subjected to a cold insult. The cold pressor is about 10 to about 15 degrees C. Any number of methods may be used for the cold pressor test, including but not limited to a cold water bath, a cold patch, cold air, and other means of reducing the plantar foot temperature through conduction, advection or radiation. The cold pressor is applied from about 1 to about 5 minutes in duration.

Imaging of the plantar and/or dorsal foot commences immediately upon removal of the cold pressor. Image collection rates are from about 10 Hz to about 60 Hz. It is preferred that both feet be in the field of view of the imaging system.

Referring now to FIGS. 5a and 5b graphs of a single plantar foot from two individuals imaged for fifteen minutes is illustrated. A single frame from the video is presented at about two minute intervals.

Image and Data Analysis:

Temporal changes for any location on the foot plantar gives an indication of a patient's auto-thermoregulation and neuronal function. FIGS. 5a and 5b illustrate the percentage recovery over a period of about five minutes for a neuropathic patient and a control given the same conditions described above. In this case, the control, in other words non-diabetic, has a recovery that is much greater than the neuropathic, diabetic patient for four locations (as sampled) on the plantar foot.

A normative model, depicted in FIG. 9, is created by performing this experiment of a sample of about 1000 or more diabetics, about 1000 or more controls, and about 1000 or more neuropathic subjects. A statistical model shows the variance of the recovery for a multiple set of locations on the foot plantar for each class of subject. The result is a risk indicator for functional deficiency where the risk is calculated based on the recovery rate at various locations on the plantar foot.

A second type of analysis is the characterization of the spatial-temporal changes in the foot temperature. FIG. 6a illustrates a control subject and FIG. 6b illustrates a neuropathic subject's thermal recovery measurement over a period of about 15 minutes. There are numerous methods that can be applied to analyze and characterize differences in recovery patterns for normals, non-risk, and pathological, low to medium risk, diabetics. These are not limited to segmentation to locate the number of closed isotherms, principle component analysis, independent component analysis, amplitude modulation—frequency modulation analysis, and others.

In segmentation, one may use one of several techniques, including local thresholding, level sets, and others to locate closed areas of constant or similar temperature. Note that the neuropathic subject will present with several isolated regions of localized constant temperature, or isotherms. The normal control subject shows no close regions of constant temperature.

With principle component analysis, the number of components needed to account for the variance in the neuropathic subject would be larger than the principle components in the control subject. With sufficient samples, a model establishes the nature of the components for each of the classes of subjects, or establishes a correlation between the number of components to account for, as an example, about 99% of the variance.

Example, referring now to FIG. 6 shows the results from one cold pressor test experiment with an age-matched control and a neuropathic subject, i.e. diagnosed peripheral neuropathy is illustrated. FIG. 6 shows video frames for pre-cold pressor (first frame), immediately after removal of the cold pressor, then time intervals out to about 15 minutes.

A form of principle component analysis was performed on individual time slices of the video. Visually, one can observe the nearly homogeneous nature of the recovery for the normal control (top row). This visual observation is reflected in the need for fewer eigenvalues to represent the near homogeneous nature of the image. Conversely, the neuropathic subject (bottom row) shows uneven spatial recovery. This is reflected in a greater number of eigenvalues needed to represent the heterogenous characteristics of the plantar foot.

Figure 10:
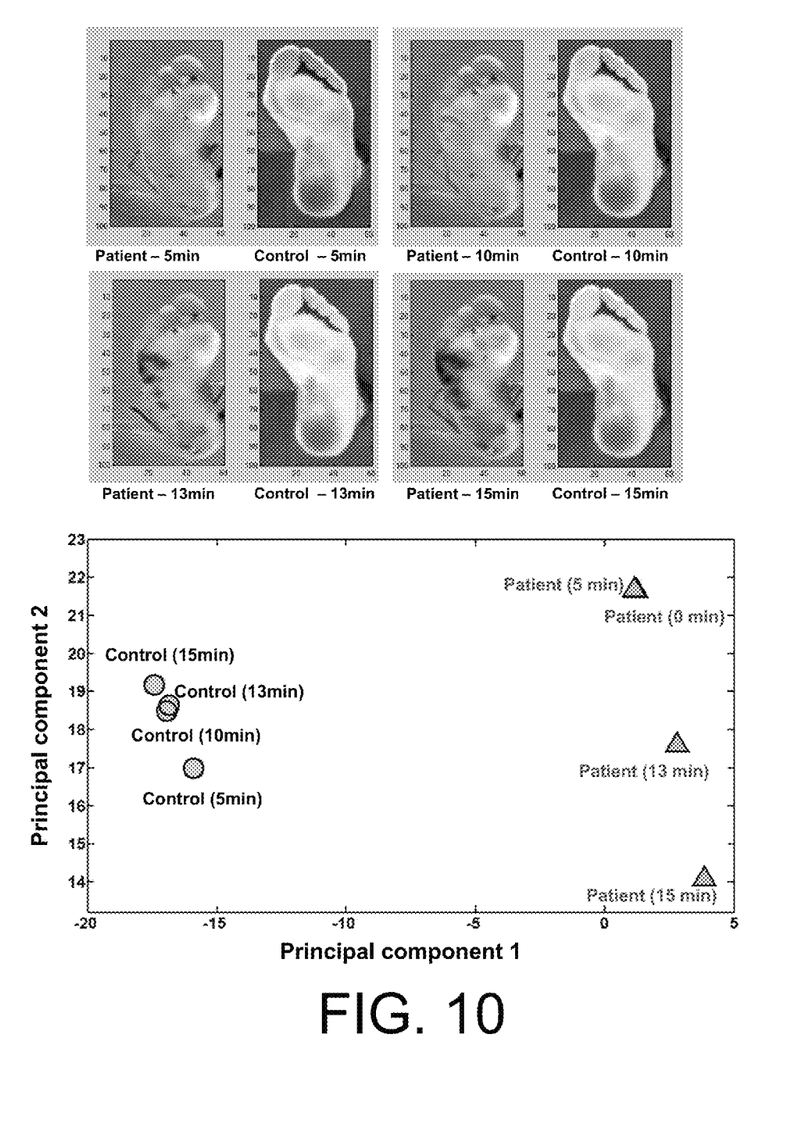
FIG. 10 shows images of a patient's foot and a control's foot post cold pressor test and a graph showing components of the patient's foot and control's foot.

The original images of approximately 650×400 pixels were down sampled, but they can be processed in their original size or any other smaller format to improve or optimize computer processing time. Additionally, images are normalized by subtracting the initial image at time zero, i.e. immediately after removal of cold pressor. FIG. 10 shows the normalized images for about 5 min., about 10 min., about 13 min. and about 15 min.

One method of an embodiment of the present invention preferably comprises:
1) Normaling the images according to the initial frame at time 0 minutes after removal of cold pressor.
2) Converting to grayscale the images from the pseudocolor thermal images.
3) Resizing the images as necessary to improve computational accuracy, complexity, and speed.
4) Vectorizing the information of the images (4 images for neuropathic, 4 images for controls).
5) Applying Principal Component Analyses and taking the components necessary to account ≥90% of the variance.
6) Plotting the vectors for about 8 video frames spaced for about 5 to about 15 minutes for the first few (approximately three) Principal Component Analyses components.

One can observe from FIG. 10 that a neuropathic patient and a control have different orientations. The control has more similarity and this is why their vectors are very close together. This method is one of the basis for the peripheral neuropathy risk analyzer.

A method of this embodiment of the present invention is applied to an empirically derived data set. Various techniques can be applied to develop the risk factor for peripheral neuropathy. A simple clustering technique, linear or non-linear regression, partial least squares, a self organizing neural network, or other related classification technique is used to assign a risk factor to the thermal emission features, such as rate of recovery, variance from the exponential recovery function, spatial variation of the recovery for different time points in the video, and other recovery characteristics.

The preceding example can be repeated with similar success by substituting the generically or specifically described reactants and/or operating conditions of this invention for those used in the preceding examples. The invention is not limited by the examples as the examples are provided to further illustrate embodiments of the present invention.

Embodiments of the present invention comprise a medical risk assessment system comprising a cold pressor applicator, a foot rest to minimize foot movement, fiducials to mark locations on the feet to facilitate tracking of movements, an infrared imager arranged to image the plantar for both feet essentially simultaneously, a signal and image capture system in communication with the imager to receive raw images from said imager, a foot local region tracking system, such as a software algorithm to track automatically features on the plantar foot and register all the frames within a video, and a peripheral neuropathy risk analyzer system to evaluate a stage or risk of the disease which is calculated using a normative model derived from the processed data, such as the recovery rate or the spatial-temporal patterns of the thermal recovery. The cold pressor applicator preferably cools the foot to a pre-specified temperature and facilitates immediate thermal imaging upon its removal. The infrared imager comprises of an infrared detector. The image and signal processor is a computer executing a risk analysis algorithm. The foot rest preferably stabilizes the feet to minimize foot movement that can add unnecessary computational burden to the tracking software, and keeps the feet within the field of view of the imager. The tracking software algorithm preferably identifies the precise location of a point on the plantar foot for each frame collected by the imager. The recovery rate after cold pressor application represents the thermoregulation of the foot as mediated by neuronal function. A recovery characteristic, rate, magnitude, and other temporal features are indicated as an index or risk factor for peripheral neuropathy. A recovery spatial pattern is indicative of risk for peripheral neuropathy.

An embodiment of the present invention comprises a peripheral neuropathy risk assessment system that detects abnormality which is directed to a probability, a stage, a category, or other indicator as to the degree of progression of the disease.

According to one embodiment of the present invention, a temporal response is dictated by the bio-heat equation suggested by Pennes. The temporal and spatial responses are indicative of efficacy of any intervention. The temporal and spatial responses are preferably measured longitudinally to determine progression or regression of the neuronal function. The temporal and spatial responses can be implemented in a screening environment to produce triage patients at risk for peripheral neuropathy.

One embodiment of the present invention uses a temperature measuring device to detect regions of thermal emission variations of the plantar and/or doral surfaces of the foot. A sufficient number of thermal detectors are preferably geometrically spaced to allow for imaging of both the dorsal and plantar regions of the foot.

A system of this embodiment identifies specific plantar and dorsal thermal emissions that have been converted to equivalent black body temperatures in order to provide an easy to understand visual-based comparison between the feet. The system creates a quantitative stratification of risk for peripheral neuropathy based on measureable quantities of temporal rate of recovery and spatial variations in recovery. The system can be used by medical technicians and other foot care specialists because the risk assessment by age and gender, for example, is standardized through a normative model that is empirically based and supported by statistical power.

In another embodiment of the present invention, an automatic output specifies the risk for peripheral neuropathy as low, suspect (i.e., medium), or high. This output is easily interpreted by the user and relates the risk to a specific referral, e.g. low suggests a repeat of the recommended annual exam, suspect suggests no immediate risk of peripheral neuropathy implying more intense monitoring and education and awareness as the intervention. High risk implies an immediate referral to a foot or diabetes specialist.

In one embodiment of the present invention a system identifies specific regions of abnormal variations in the recovery temperature of the plantar or dorsal foot areas, caused by abnormal neuronal function. These recovery variations are based on the temporal and spatial processing of the thermal emissions measured over the time course of the procedure. Pseudocolor images that represent thermal emission variations are preferably produced.

Note that in the specification and claims, "about" or "approximately" means within twenty percent (20%) of the numerical amount cited. All computer software disclosed herein may be embodied on any computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of detecting a neuronal health of a patient's foot comprising the steps of:
    selecting a patient's foot to thermally monitor;
    obtaining a pre-treatment temperature of the patient's plantar foot being monitored;
    applying a cold pressor to an entire surface of the plantar foot of the patient for a predetermined amount of time to lower a temperature in the patient's foot to a temperature of between about 90° F. and 75° F.;
    removing the cold pressor from the patient's foot;
    obtaining a plurality of images of the patient's foot using an infrared imager having a data acquisition rate of at least 10 Hz to capture an increase of surface temperature of the patient's foot over a pre-determined amount of time after the cold pressor is removed from the patient's foot to measure a spatial and a temporal recovery of a thermal signal;
    registering the plurality of images obtained;
    determining a rate and a change in rate of temperature recovery of the patient's entire surface of the plantar foot during the first minute following cold pressor removal by determining a thermal measurement as a function of time at an initial thermal temperature minus an exponential function at a time, t, and for recovery factor K and determining a thermal recovery signal for the patient's entire surface of the plantar foot for a pre-determined period of time; and
    comparing with an appropriately programmed processor the rate and the change in rate of temperature recovery of the patient's entire surface of the plantar foot at the first minute and the thermal recovery signal at the pre-determined period of time to the same measurements obtained for a control patient's foot to determine the neuronal health of the patient's foot being thermally monitored.

2. The method of claim 1 wherein the registering step comprises aligning a fiduciary within each image for use in co-registration of image frames.

3. The method of claim 1 wherein the infrared imager comprises an infrared detector.

4. The method of claim 1 further comprising using a temperature measuring device to detect regions of thermal emission variations of the plantar of the foot.

5. The method of claim 1 wherein the obtaining a plurality of images step occurs immediately after the cold pressor is removed from the foot.

6. The method of claim 1 wherein the plurality of images is obtained in an approximately 900 nm to 15 μm spectral range.

7. The method of claim 1 wherein the rate and change in rate of temperature recovery of the patient's entire surface of the plantar foot during the first minute is compared to a rate and change in rate of a thermal recovery from a population of patients comprising two or more stages of neuropathy in order to determine if the patient's foot thermally monitored has a neuropathy.

8. The method of claim 1 wherein the pre-determined time is less than 15 minutes.

9. A method of detecting a neuronal health of a patient's foot comprising:
    selecting a patient's foot to thermally monitor;
    obtaining a pre-treatment temperature of the patient's foot being monitored;
    applying a cold pressor to an entire surface of the plantar foot of the patient for a predetermined amount of time to reduce a temperature in the patient's foot to between about 90° F. and 75° F.;

removing the cold pressor from the patient's foot;
obtaining a plurality of images of the patient's foot using an infrared imager having a data acquisition rate of at least 10 Hz to capture an increase of surface temperature of the patient's foot over a pre-determined amount of time which is less than a time for recovery to a pre-treatment temperature after the cold pressor is removed from the patient's foot to generate a thermal and a temporal recovery signal;
registering the plurality of images obtained;
determining with an appropriately programmed processor a principal component analysis a number of principle components needed to account for any variance in the thermal recovery signal over time from the registered plurality of images; and
classifying the neuronal health of the patient's foot thermally monitored as abnormal based upon an increase in the number of principal components required to account for greater than a pre-determined percentage of the variance in the thermal recovery signal when compared to the number of principal components required to account for greater than the pre-determined percentage of the variance in a thermal recovery signal of a control patient's foot.

10. The method of claim 9 wherein the step of determining the number of principle components needed to account for a variance in the thermal recovery signal occurs at a pre-determined time that is prior to the time for recovery to a pre-treatment temperature.

11. The method of claim 9 wherein the step of classifying the neuronal health of a patient's foot further comprises identifying the number of principal components required to account for the variance in the thermal recovery signal for the patient's foot being thermally monitored and comparing to a principal components from a population of patients comprising two or more stages of neuropathy.

12. The method of claim 9 wherein the pre-determined time is less than 15 minutes.

* * * * *